United States Patent
De Ferra et al.

(10) Patent No.: US 10,870,711 B2
(45) Date of Patent: Dec. 22, 2020

(54) PROCESS FOR THE PREPARATION OF POLYSACCHARIDES

(71) Applicant: Chemi S.P.A., Cinisello Balsamo (IT)

(72) Inventors: Lorenzo De Ferra, Patrica (IT); Ettore Ammirati, Patrica (IT); Simona Andreassi, Patrica (IT); Mauro Annibaldi, Patrica (IT); Luca Mandelli, Patrica (IT); Barbara Pinto, Patrica (IT); Felice Stracqualursi, Patrica (IT)

(73) Assignee: Chemi S.P.A., Cinisello Balsamo (IT)

( * ) Notice: Subject to any disclaimer, the term of this patent is extended or adjusted under 35 U.S.C. 154(b) by 0 days.

(21) Appl. No.: 15/570,227

(22) PCT Filed: May 18, 2016

(86) PCT No.: PCT/EP2016/061088
§ 371 (c)(1),
(2) Date: Oct. 27, 2017

(87) PCT Pub. No.: WO2016/184887
PCT Pub. Date: Nov. 24, 2016

(65) Prior Publication Data
US 2018/0134813 A1 May 17, 2018

Related U.S. Application Data

(60) Provisional application No. 62/164,240, filed on May 20, 2015.

(30) Foreign Application Priority Data

May 20, 2015 (IT) .................. 102015000016209

(51) Int. Cl.
*C08B 37/00* (2006.01)
*C07H 11/00* (2006.01)
*A61K 31/737* (2006.01)

(52) U.S. Cl.
CPC ........ *C08B 37/0057* (2013.01); *A61K 31/737* (2013.01); *C07H 11/00* (2013.01); *C08B 37/0003* (2013.01)

(58) Field of Classification Search
CPC ............ C08B 37/0003; C08B 37/0057; A61K 31/737; C07H 11/00
USPC ........................................................ 536/123
See application file for complete search history.

(56) References Cited

U.S. PATENT DOCUMENTS 2,689,848 A    9/1954 Elfriede et al.

FOREIGN PATENT DOCUMENTS

| WO | 2008107906 A1 | 9/2008 | |
|---|---|---|---|
| WO | 2014114723 A1 | 7/2014 | |
| WO | WO 2014/114723 A1 * | 7/2014 | ............. C08B 37/00 |

OTHER PUBLICATIONS

Teleman et al, Carbohydrate Research, 2000, 329, 807-815.*
Moine et al, J. Nat. Prod. 2007, 70, 60-66.*
Choudhary et al, ACS Catalysis, 2011, 1, 1724-1728.*
Chen X, et al., "Kinetics and mechanism of autohydrolysis of hardwoods.", Bioresource Technology 101 (2010) 7812-7819.
Daus S.,et al., "Homogeneous sulfation of xylan from different sources," Macromol. Mater. Eng. 2011, 296, 551-561.
Degenhardt M., et al., "Quality control of pentosane polysulfate by capillary zone electrophoresis using indirect detection," Journal of Chromatography A 817 (1998) 297-306.
Froschauer C., et al., "Separation of hemicellulose and cellulose from wood pulp by means of ionic liquid/cosolvent systems," Biomacromolecules 2013, 14, 1741-1750.
Goncalves V. M. F., et al., "Structural characterization of the acetylated heteroxylan from the natural hybrid Paulownia elongata/ Pauwlonia fortunei," Carbohydrate Research 343 (2008) 256-266.
Hagglund E., et al., "Dimethylsuphoxide, a solvent for hemicellulose," Acta Chemica Scandinavica 10 (1956) 1160-1164.
Search Report and Written Opinion of PCT/EP2016/061088 dated Jul. 14, 2016.
Shi Cheng Zhang, et al., "Study on the process of extracting xylan," Advanced Materials Research, vol. 183-185, Jan. 1, 2011 pp. 1952-1955.

(Continued)

*Primary Examiner* — Ganapathy Krishnan
(74) *Attorney, Agent, or Firm* — Silvia Salvadori, P.C.; Silvia Salvadori

(57) ABSTRACT

The present invention relates to a process for the preparation of a polysaccharide composed of D-xylose units of formula (III) linked together via beta 1,4 glycosidic bonds wherein $R_1$ is hydrogen or acetyl, $R_2$ is hydrogen, acetyl or a 4-O-methyl glucuronic acid unit, wherein, when $R_2$ is a 4-O-methyl glucuronic acid unit, the $R_1$ group on the same saccharide unit is defined as G, wherein G is hydrogen or acetyl, and wherein the sugar unit at the reducing end of sun such polysaccharide is xylose, lyxose or xylulose, said process comprising the following steps: selective deacetylation of xylan extracted from beech wood; and isomerization of the selectively deacetylated xylan achieved in step or the following steps: isomerization of xylan extracted from beech wood; and selective deacetylation of isomerized xylan achieved in step. The process is useful for the preparation of pentosan polysulfate or pharmaceutically acceptable salts thereof for pharmaceutical use.

14 Claims, 1 Drawing Sheet

(56) References Cited

OTHER PUBLICATIONS

Xin L., et al., "New insights on monosaccharides isomerization, dehydration and fragmentation in hot-compressed water," Journal of Supercritical Fluids, vol. 61, Sep. 17, 2011 pp. 146-156.
Li X-C, et al., "One-pot catalytic conversion of xylose to furfural on mesoporous niobium phosphate", Acta Physico-Chimica Sinica, vol. 28 No. 10, pp. 2349-2354.
Office Action dated Jul. 11, 2019 in corresponding Chinese Application No. 201680028390.0.

* cited by examiner

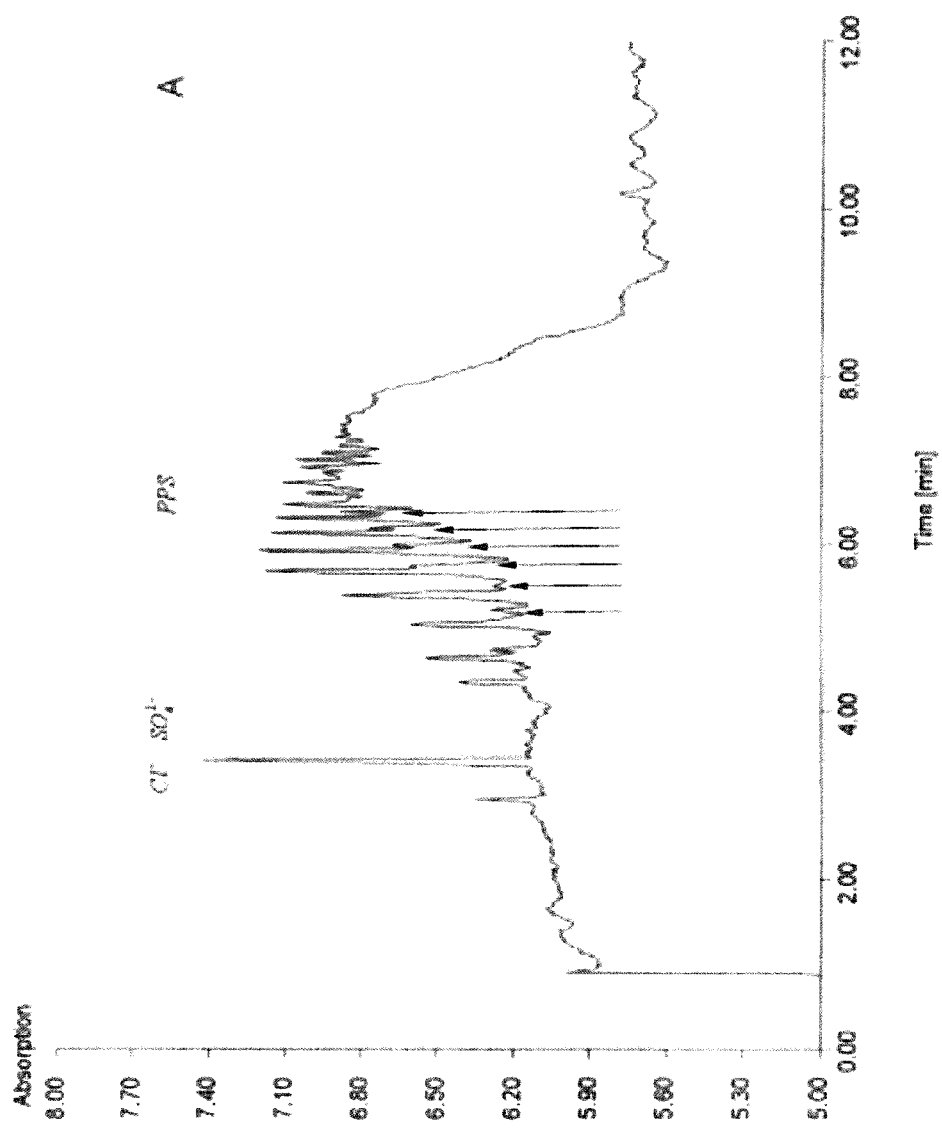

PROCESS FOR THE PREPARATION OF POLYSACCHARIDES

This application is a U.S. national stage of PCT/EP2016/061088 filed on 18 May 2016, which claims priority to and the benefit of U.S. Provisional Application No. 62/164,240 filed on 20 May 2015 and claims priority to and the benefit of Italian Application No. MI2015000016209 filed on 20 May 2015, the contents of which are all incorporated herein by reference in their entireties.

Polysaccharides have a widespread occurrence among natural products and manifest several and useful biochemical properties that are more and more attracting interest for medical uses.

As examples, properties of some polysaccharides as immunomodulatory or antitussive agents are the subjects of several scientific reports.

The presence of specific structural elements like branching, acetyl groups and rare sugar units could impact on the biochemical and potential pharmacological properties of these polysaccharides and of the derivatives that can be synthetized therefrom.

Between such derivatives, pentosan polysulfate is of special importance.

Several pharmaceutical products contain pentosan polysulfate or a salt thereof as active ingredient. As an example, Elmiron®, that is sodium pentosan polysulfate having a high sulfation degree and a molecular weight of 4000-6000 Dalton, is authorized in USA for the treatment of Interstitial Cystitis.

From a structural point of view, pentosan polysulfate is described as a complex mixture of sulfated polysaccharidic chains having sulfated β-(1→4)-D-xylopyranose (hereinafter, xylose unit) as the most recurrent repetitive unit.

Sulfated 4-O-methyl α-D-glucopyranosyl uronic acid units (hereinafter, methyl glucuronic acid units) bonded to position 2 of xylose units are also present.

The structural formula of pentosan polysulfate or salts thereof as reported in technical and scientific literature is depicted in formula (I):

acid in the presence of pyridine to obtain sulfuric acid ester salt of xylan, followed by oxidative depolymerisation in acidic or neutral aqueous medium to obtain a depolymerised product, which is dialyzed and fractionated to obtain the desired product. However, said process does not provide an end product with desired molecular weight profile. Moreover, said process is tedious, costly and provides pentosan polysulfate in low yield.

WO2008107906 discloses a process for similarly producing sodium pentosan polysulfate, which involves the use of a nanofiltration membrane system for purification of crude depolymerised pentosan polysulfate.

Differences in the manufacturing process can result in molecular differences of pentosan polysulfate, such as branching, degree of sulfation, position of the sulfate groups on the polysaccharidic chain and average molecular weight.

It is well known that the clinical efficacy of sulfated carbohydrates can be affected by said differences, such as type and position of —$SO_3$— groups. Hence, the need to fully control and characterize the molecules is felt.

Manufacturing processes for pentosan polysulfate for pharmaceutical use shall guarantee that all the structural elements recognized in pentosan polysulfate contained in pharmaceutical products are conserved in order to ensure the precise pharmacological profile, therapeutic efficacy and safety of the same. This is in line with the requirements from the USA Food and Drug Administration (FDA) for the authorization of generic versions of drugs of complex composition like Elmiron®; in fact, for these applications, the documented evidence that the generic candidate has the same chemical, physical and immunochemical characteristics of the Reference Listed Drug is requested.

Nevertheless, the complete structural characterization of pentosan polysulfate contained in pharmaceutical products, such as Elmiron®, has not been fully evaluated or disclosed yet.

By means of the in depth structural studies described in patent application WO2014114723, it has been possible to identify specific structural elements of pentosan polysulfate contained in pharmaceutical products on the market. In

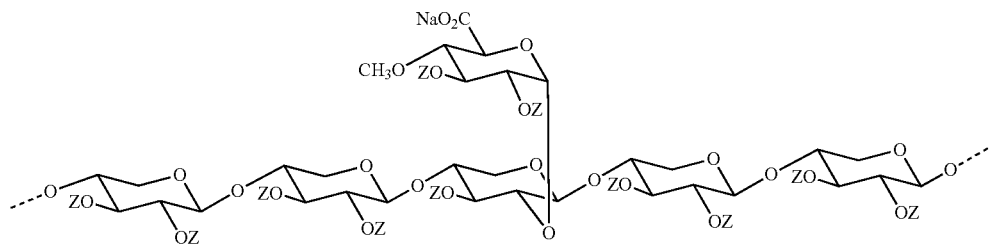

(I)

wherein Z represents —$SO_3Y$, and Y is at least one member selected from the group consisting of H and a pharmaceutically acceptable cation, such as sodium or calcium.

Pentosan polysulfate is a semi-synthetic product, which may be achieved by treating xylan extracted from beech wood or other plant sources with sulfating agents, such as chlorosulfonic acid or sulfuryl chloride. After sulfation, pentosan polysulfate is usually treated with sodium hydroxide to yield the corresponding sodium salt.

Pentosan polysulfate is disclosed in U.S. Pat. No. 2,689,848. Said patent discloses a process for producing pentosan polysulfate comprising treating xylan with chlorosulfonic particular, by analyzing pentosan polysulfate isolated from pharmaceutical products on the market, such as Elmiron®, it has been shown the presence of acetylated monosaccharide units.

In particular, it was possible, by combining several NMR techniques such as analysis HSQC, HMBC, TOCSY and COSY, to find that the acetyl groups are not equally distributed between the positions 2 and 3 of the repeating units which constitute pentosan polysulfate, but are mainly present at position 3 of the repeating units of xylose. Furthermore in WO2014114723 was found that said acetyl groups are mainly bound to the position 3 of the xylose units which have also a 4-0-methyl-glucuronic acid unit in position 2.

The amount of O-acetyl groups in pentosan polysulfate, i.e. the degree of acetylation, is thus another important feature that should be taken into consideration when manufacturing pentosan polysulfate for pharmaceutical use, in order to ensure the precise pharmacological profile, therapeutic efficacy and safety of the same.

NMR spectroscopy has demonstrated to be a very useful analytical technique in the field of the structural characterization of polysaccharides and sulfated polysaccharides; some specific signals can be used for assessing the presence of specific structural elements in pentosan polysulfate. For example the presence of the signal at about 2.3 ppm in the $^1$H NMR spectrum and the signal at 5.25/75.96 ppm in the HSQC NMR (heteronuclear single quantum coherence NMR) confirms the presence of the acetyl group on the oxygen in position 3 of the xylose units bonded to the methyl glucuronic acid units, instead of the sulfate group —SO$_3$Y depicted in formula (I), as above mentioned.

The present inventors have verified that the structure of pentosan polysulfate isolated from pharmaceutical products containing pentosan polysulfate, such as Elmiron®, is characterized by further structural elements that have not so far been identified or described, and which may be correlated to the therapeutic efficacy and safety of pentosan polysulfate for pharmaceutical use.

In particular, by analyzing the capillary electrophoresis electropherograms (CE electropherograms) of pentosan polysulfate isolated from pharmaceutical products containing pentosan polysulfate, such as Elmiron®, the inventors have verified the presence of satellite signals close to the most abundant peaks. Satellite peaks are also present in the electropherogram reproduced in FIG. 2 of Wätzig et al. Journal of Chromatography A (1998), 817, 297, wherein the added arrows indicate the satellite peaks, herein reported as FIG. 1.

The most abundant peaks should correspond to the pentosan polysulfate chains having sulfated xylose units at the reducing end, while the satellite signals should correspond to a modified pentosan polysulfate chains, wherein the sulfated xylose unit at the reducing end is substituted by a sulfated isomer of xylose. Such an isomer may be lyxose or xylulose.

Thus, the pentosan polysulfate isolated from pharmaceutical products such as Elmiron®, which displays the satellite peaks in the electropherograms, should include at the reducing ends lyxose units, xylulose units or both of them.

Pentosan polysulfate for pharmaceutical use may be obtained by sulfation reaction of an appropriate polysaccharide, such as Elmiron®, to be definitely reflected in the finally synthetized and isolated pentosan polysulfate.

The sulfonation reaction occurs on free —OH groups of the polysaccharide chain units without affecting the above mentioned structural elements of the polysaccharide.

Therefore, there exists a need to develop an improved manufacturing process for an appropriate polysaccharide having all the structural elements recognized in the pentosan polysulfate available on the market, which appropriate polysaccharide may be used as starting material for achieving, by sulfation, pentosan polysulfate having all the structural elements recognized in pentosan polysulfate contained in pharmaceutical products.

It is an object of the present invention a process for the preparation of a polysaccharide composed of D-xylose units of formula (III) linked together via beta1,4 glycosidic bonds

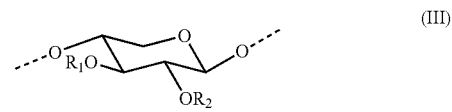

(III)

wherein

R$_1$ is hydrogen or acetyl,

R$_2$ is hydrogen, acetyl or a 4-O-methyl glucuronic acid unit, wherein, when R$_2$ is a 4-O-methyl glucuronic acid unit, the R$_1$ group on the same saccharide unit is defined as G, wherein G is hydrogen or acetyl, and wherein the sugar unit at the reducing end of such a polysaccharide is xylose, lyxose or xylulose, said process comprising the following steps:

a) selective deacetylation of xylan extracted from beech wood; and b) isomerization of the selectively deacetylated xylan achieved in step a)

or the following steps:

c) isomerization of xylan extracted from beech wood; and d) selective deacetylation of isomerized xylan achieved in step c).

The above described meanings of R$_1$ and R$_2$, may be selected in a saccharide unit independently from the meanings of R$_1$ and R$_2$ in the others saccharide units.

It is another object of the present invention a process for the preparation of a polysaccharide of formula (II)

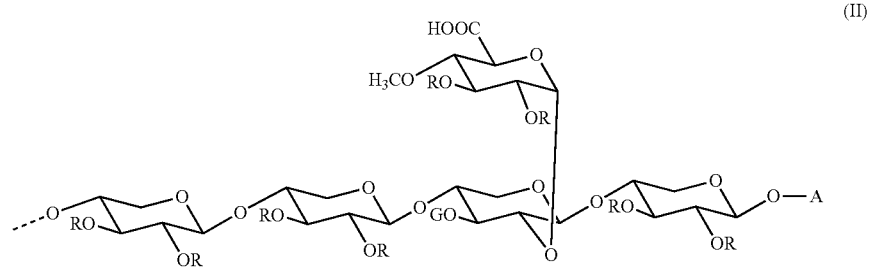

(II)

ride which, besides the requirements of purity, molecular weight distribution and degree of acetylation suitable to the scope, already has in its structure all the above mentioned structural elements recognized in pentosan polysulfate isolated from pharmaceutical products containing pentosan wherein R is hydrogen or acetyl G is hydrogen or acetyl A is a xylose, lyxose or xylulose unit, said process comprising the following steps, above already cited:

a) selective deacetylation of xylan extracted from beech wood; and b) isomerization of the selectively deacetylated xylan achieved in step a)

or the following steps:

c) isomerization of xylan extracted from beech wood; and d) selective deacetylation of isomerized xylan achieved in step c).

The polysaccharide object of the present invention is constituted of a mixture of components differing each other in their chain length, in their substitution (represented in formula (II) by R and G groups), in the sugar unit at the reducing end (represented in formula (II) by A group), and in the position of 4-O-methyl glucuronic acid units, exemplificatively represented in formula (II).

Xylan may be extracted from beech wood by different procedures known in the art. One limitation that must be taken into consideration is that strongly alkaline extraction conditions must be avoided. This is to avoid the complete removal of all the acetyl groups of xylan, that otherwise would occur. For this reason, it is not recommended to follow the procedures frequently reported in literature which are based on the extraction with sodium hydroxide concentrated solution or the analogue procedure in which concentrated potassium hydroxide is used.

Suitable extraction methods which may be conveniently used are the hot water extraction (see for example X. Chen et al. Bioresource Technology (2010),101,7812), the xylan extraction with DMSO from beech wood previously subjected to delignification (E. Hägglund et al. Acta Chemica Scandinavica (1956), 10, 1160 and D. V. Evtuguin et al. Carb. Res. (2008), 343, 256) and the procedures based on xylan extraction with ionic liquids (see for example R. C. Sun et al. Bioresources (2013), 8, 1946 and C. Froschauer et al. (2013), 14, 1741).

Selective deacetylation of xylan extracted from beech wood is performed to cleave the exceeding acetyl groups.

Selective deacetylation is a necessary step of the process, being the degree of acetylation of beech xylan extracted with these procedures higher than that found in pentosan polysulfate isolated from the pharmaceutical products available on the market.

It has been surprisingly found that it is possible to remove in a selective manner most of the acetyls of the of $R_1$ (when $R_2$ in the same sugar unit is not a 4-O-methyl glucuronic unit), $R_2$ and R groups while preserving at the same time many of the G groups in formula (III) or (II) as acetyl.

Selectively deacetylated xylan achieved in step a) or in step d) is characterized in that at least 20% of the G groups in formula (III) or (II) are acetyl; preferably from 35% to 70% of the G groups in formula (III) or (II) are acetyl.

Selectively deacetylated xylan achieved in step a) or in step d) is also characterized in that at least 50%, and preferably at least 70%, of the total acetyl groups are present on G groups in formula (III) or (II). Step a) or step d) may be performed in basic or mildly basic reaction conditions in the presence of a basic reagent in aqueous environment.

Preferably, the selective deacetylation is performed in the pH range between pH=8 and pH=12; more preferably between pH=9 and pH=11.

Suitable basic reagents are aqueous solutions of alkaline or alkaline terrous hydroxides; preferably, the basic reagent is a sodium hydroxide aqueous solution.

The selective deacetylation of step a) or that of step d) may be carried out adding the basic reagent to the mixture of xylan extracted from beech wood in water.

The addition of the basic reagent is preferably carried out at constant pH conditions (i.e. pHstat setting), preferably automatically controlling the addition rate of the basic reagent by the measure of pH of the reaction mixture in such a way that the pH value is never allowed to deviate excessively from the set value, either in the direction of lower pH values for the release of acetic acid from the xylan substrate or toward the higher values due to excessive basic reagent addition (i.e. pHstat control).

The reaction is performed at a temperature between 0° C. and 100° C., preferably between 0° C. and 25° C.

Reaction duration may vary from 0.5 to 12 hours, preferably between 4 to 10 hours, strongly depending on the adopted reaction conditions.

Control of the amount of basic reagent necessary to maintain over time the selected reaction pH is a convenient method to monitor the reaction progression when the transformation is carried out under constant pH conditions.

Further, the progression of the reaction and the reaction selectivity may be conveniently monitored by means of $^1$H NMR spectroscopy observing in particular the signals in the range between 2.0 ppm and 2.5 ppm, where the separate signals corresponding to the different acetyl groups are found.

Isolation of the selectively deacetylated xylan at the end of step a) or at the end of step d) may be accomplished following the methods reported in the technical and scientific literature. For instance, precipitation by addition of organic solvents like methanol and/or ethanol. In alternative, procedures based on ultrafiltration followed by lyophilization can also advantageously be carried out.

In step b) or in step c) some of the xylose units at the reducing end of the polysaccharide chains are isomerized into lyxose or xylulose units.

Isomerization should be performed in reaction conditions that avoid complete deacetylation of xylan. Therefore, too severe basic conditions are to be avoided.

Step b) or step c) may be carried out by heating the selectively deacetylated xylan achieved in step a) or the xylan extracted from beech wood in pyridine for a sufficient time. Pyridine can be used in anhydrous form or in presence of water up to a water content of 80%. Water content can also vary during the reaction time if, in the course of the isomerization, solvent is distilled off from the reactor.

Total volume of pyridine and water in respect to xylan may be between 2 to 40 volumes, preferably between 4 to 20 volumes.

Reaction time may vary from 4 and 12 hours.

Reaction temperature may vary between 70 and 150° C. If reaction is carried out at reflux temperature, the reaction temperature will vary, as a function of water content, between 94 and 115° C.

In one embodiment, 1 g the selectively deacetylated xylan achieved in step a) or 1 g of the xylan extracted from beech wood may be dissolved in 5 mL of water and 5 mL of pyridine and heated to reflux for 8 hours.

The reaction time can be reduced in the presence of at least one additional substance selected from alumina or a substance containing polyvalent metals, such as aluminum or calcium compounds. The preferred aluminum compound is aluminum acetate. Preferred calcium compounds are calcium chloride and calcium acetate.

The amount of these additional compound, referred to the xylan quantities, can conveniently be comprised between 10 to 100% by weight, preferably between 20 to 50% by weight.

In a further embodiment, 1 g the selectively deacetylated xylan achieved in step a) or 1 g of the xylan extracted from beech wood may be dissolved in 5 mL of water and 5 mL of pyridine; 0.2 g alumina are added and the mixture is heated to reflux for 5 hours.

The isolation can be carried out anhydrifying by azeotropic water removal the reaction mixture, if necessary, followed by addition of ethanol. The precipitate xylan is separated by filtration and dried.

The isomerization of the xylose units at the reducing end of polysaccharide chains of selectively deacetylated xylan achieved in step a) or at the reducing end of polysaccharide chains of the xylan extracted from beech wood is carried out without altering the polymeric structure of said xylans; that is, by maintaining substantially unchanged the number of xylose units and the methyl glucuronic acid units in the polysaccharidic chains. This is demonstrated by comparing the molecular weight profile of the deacetylated xylan achieved in step a) with that of the polysaccharide of formula (III) or (II) achieved after the isomerization step b).

In a further embodiment, steps a) and b) of the process of the present invention are carried out in "one-pot", reacting the xylan extracted from beech wood by means of an acetyl preserving method; it can be accomplished using a basic reagent in presence of at least one substance containing polyvalent metals, in aqueous environment.

Suitable basic reagents are aqueous sodium hydroxide, aqueous calcium hydroxide; preferably, the basic reagent is aqueous sodium hydroxide.

Suitable substances containing polyvalent metals are calcium chloride, calcium acetate and aluminum compounds such as aluminum acetate.

Reaction conditions are similar to the reaction condition suitable for selective deacetylation with the difference that the polyvalent metal containing substance is added to the reaction mixture since the beginning of the reaction. Its amount may be up to 30% by weight in respect to the substrate, preferentially not more than 20% by weight.

The addition of the basic reagent is preferably carried out at constant pH conditions (i.e. pHstat setting), gradually adding the basic reagent while controlling the pH (i.e. pHstat control).

In one embodiment, the one-pot selective deacetylation and isomerization of steps a) and b) may be carried out in the presence of aqueous calcium hydroxide or aqueous sodium aluminate, in this way providing at the same time the basic reagent and the substance containing polyvalent metals.

Isolation of the so obtained xylan can be conveniently accomplished following the methods reported in the technical and scientific literature. For instance, precipitation by addition of organic solvents like methanol and/or ethanol. In alternative, procedures based on ultrafiltration followed by lyophilization can also be advantageously carried out.

A further aspect of the present invention is represented by the polysaccharide of formula (III) or (II) obtainable through the aforementioned process.

The aforementioned process may further include the conversion of the polysaccharide of formula (III) or (II) into pentosan polysulfate by sulfation reaction.

The sulfation reaction may be carried out by the procedures known in the art, such as the procedure disclosed in Daus et al. (2011), Macromolecular Materials and Engineering, 296, pages 551-561, wherein xylan extracted from beech wood is used as starting material.

Thus, another aspect of the present invention is the pentosan polysulfate obtainable through the aforementioned process.

The aforementioned process may further comprise the step of converting pentosan polysulfate into a pharmaceutically acceptable salt, preferably an alkali metal or alkaline earth salts, by treatment of pentosan polysulfate achieved according to the present invention with appropriate metal hydroxides, preferably with alkali or alkaline earth hydroxides such as sodium or calcium hydroxide.

Preferably, pentosan polysulfate is treated with sodium hydroxide to yield the corresponding sodium salt.

It is an object of the present invention a polysaccharide composed of D-xylose units of formula (III) linked together via beta1,4 glycosidic bonds

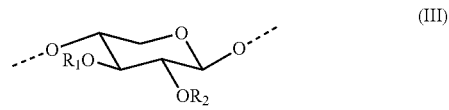

(III)

wherein $R_1$ is hydrogen or acetyl, $R_2$ is hydrogen, acetyl or a 4-O-methyl glucuronic acid unit, wherein, when $R_2$ is a 4-O-methyl glucuronic acid unit, the $R_1$ group on the same saccharide unit is defined as G, wherein G is hydrogen or acetyl, and wherein the sugar unit at the reducing end of such polysaccharide is xylose, lyxose or xylulose.

It is a further object of the present invention a polysaccharide of formula (II)

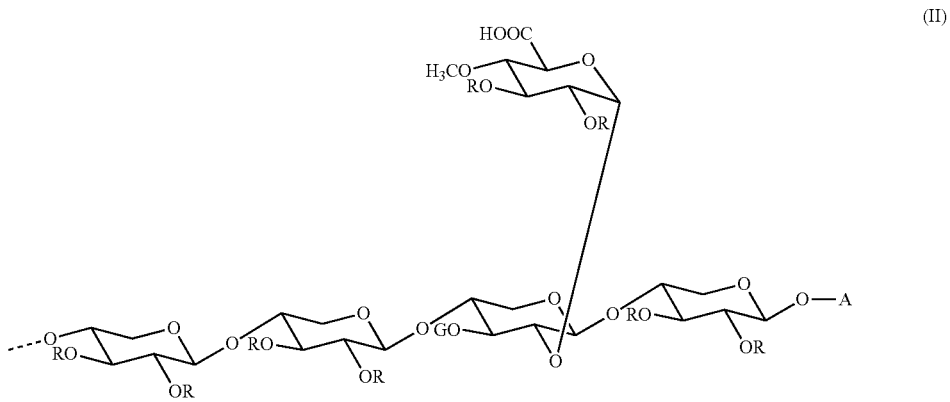

wherein R is hydrogen or acetyl,
G is hydrogen or acetyl,
A is a xylose, lyxose or xylulose unit.

The polysaccharide object of the present invention is constituted of a mixture of components differing each other in their chain length, in their substitution (represented in formula (II) by R and G groups), in the sugar unit at the reducing end (represented in formula (II) by A group), and in the position of 4-O-methyl glucuronic acid units, exemplificatively represented in formula (II).

The polysaccharides of formula (III), (II) and pentosan polysulfate achieved according to the present invention may be analyzed by means of capillary electrophoresis, HSQC NMR and $^1$H NMR to verify the presence of the characteristic structural units recognized in pentosan polysulfate isolated from pharmaceutical products containing pentosan polysulfate.

In a further aspect, the present invention thus also relates to methods for identifying the presence of the structural elements recognized in pentosan polysulfate isolated from pharmaceutical products containing pentosan polysulfate, in samples of pentosan polysulfate, as well as in the polysaccharides of formula (III) and (II) achieved according to the present invention and to their application for the preparation of pentosan polysulfate or a pharmaceutically acceptable salt thereof for pharmaceutical use.

Said methods comprise the comparison of CE electropherograms, HSQC NMR and $^1$H NMR spectra of the polysaccharide of formula (III) and (II) and/or of the pentosan polysulfate achieved according to the present invention with those of the pentosan polysulfate isolated from pharmaceutical products containing pentosan polysulfate.

Definitions

The term "pharmaceutically acceptable salts" herein refers to those salts or derivatives which possess the biological effectiveness and properties of the salified compound and which do not produce adverse reactions when administered to a mammal, preferably a human. The pharmaceutically acceptable salts may be inorganic or organic salts; examples of pharmaceutically acceptable salts include but are not limited to alkali metal or alkaline earth salts. Further information on pharmaceutically acceptable salts can be found in Handbook of pharmaceutical salts, P. Stahl, C. Wermuth, WILEY-VCH, 127-133, 2008, herein incorporated by reference.

The term "repetitive unit" refers to a part of the polymer chain which is derived from a single molecule of a monomer.

The term "one-pot" refers to two or more consecutive reactions which are carried out without isolating the respective intermediate product or products.

The term "reducing end" refers to the terminal monosaccharide of the polysaccharide chain having the anomeric carbon (C1) that is not involved in a glycosidic bond.

The term "structural element" refers to any characterizing portion of a polysaccharide chain, which may be present as single unit or as a repetitive unit in the polysaccharide chain, either regularly distributed in the chain or not. For example, a suitable structural element may be a monosaccharidic unit characterized in that it is branched, or it includes specific substituents or may be a isomer of the recurring monosaccharidic repetitive unit.

The term "pentosan polysulfate for pharmaceutical use" refers to a pentosan polysulfate having all the structural elements recognized in pentosan polysulfate isolated from pharmaceutical products on the market, such as Elmiron®. The presence of all the recognized structural elements may be verified by a comparison of the CE electropherograms and of HSQC NMR and $^1$H NMR spectra of the pentosan polysulfate for pharmaceutical use and that of the pentosan polysulfate isolated from pharmaceutical products containing pentosan polysulfate, such as Elmiron®.

All publications, patents and patent applications cited herein, are hereby incorporated by reference in their entirety.

The following examples illustrate possible realizations of the invention and cannot be used in any instance for limiting its value and field of validity.

EXAMPLES

Example 1

Method of Analysis for Acetyl Groups

Xylan sample (about 25 mg) is solubilized in 0.7 mL D2O. For the acquisition of the $^1$H-NMR spectra an Agilent Mercury –200 MHz equipment was used.

Signal attributions for the hydrogen atoms of the relevant acetyl groups are the following ones:
  2.20 ppm: Acetyl group bonded to position 3 of a xylose unit linked in position 2 with a 4-O-methyl glucuronic acid unit
  2.14 ppm: Acetyl group bonded to position 3 of a xylose unit not linked to 4-O-methyl glucuronic acid units
  2.09 ppm: Acetyl group bonded to position 2 of a xylose unit

Example 2

Method of Analysis for Monosaccharides

Xylan sample (about 25 mg) is hydrolyzed in 4 mL sulfuric acid 1M at 110° C. for 1.5 hours. After hydrolysis the mixture is neutralized with sodium hydroxide. For the derivatization 0.1 mL of the neutralized solution are mixed with 0.4 mL of 0.23 M phosphate buffer (pH=8) and 0.2 mL of a 3-methyl-1-phenyl-2-pyrazoline-5-one (PMP) 87 mg/mL solution in methanol.

The mixture is heated at 70° C. for 1 hour and extracted at room temperature three times with 0.7 mL chloroform. The derivatized solution is prepared diluting 0.1 mL of the aqueous phase with 1 mL of Phase B (see Eluents). For the HPLC analysis Aeris Peptide XB-C18 4.6×250 mm (Phenomenex) is used. The chromatographic conditions are:

| | |
|---|---|
| Flow: | 0.8 mL/min |
| Column T: | 35° C. |
| Gradient: | t = 0 min Phase A 30% Phase B 70% |
| | t = 1 min Phase A 30% Phase B 70% |
| | t = 41 min Phase A 0% Phase B 100% |
| | t = 42 min Phase A 30% Phase B 70% |
| | t = 55 min Phase A 30% Phase B 70% |
| Eluents: | Phase A = 100% Na2HPO4 buffer 0.1M pH 7 |
| | Phase B = 80% Na2HPO4 buffer 0.1M pH 7 20% acetonitrile |
| Detector: | UV 250 nm |
| Injection: | 5 µL of the derivatized soluzion |
| Retention times: | Lyxose about 25 min |
| | Xylose about 37 min |

Example 3

Extraction of Beech Xylan

Sodium hydroxide 15% solution is added until pH=4 to 270 mL of a 10% solution of peracetic acid. Beech sawdust (14 g) is added under stirring and the mixture is heated to 85° C. Stirring is maintained at 85° C. for 30 minutes. Decolorization is observed. After cooling at room temperature the mixture is filtered and the recovered solids are washed with fresh water. After drying under vacuum at 40° C., 7.5 g are obtained. To the dried product 450 mL of DMSO are added. The suspension is heated under nitrogen at 60° C. and stirred for 24 hours, cooled at room temperature and filtered. DMSO extraction is repeated on the solid. Each of the DMSO solutions are added with 2 L ethanol, cooled at 4° C. and maintained for 3 days. The solids are filtered, mixed together and dried yielding in total 0.33 g of beech xylan.

Example 4

Extraction of Beech Xylan

Xylan extraction is carried out using an accelerated solvent extractor equipment (Dianox ASE 150 model from Thermo Scientific). The 100 mL stainless steel cell of the instrument is charged with 30 g of beech sawdust. Deionized water is used as extraction solvent. The following instrumental parameters are applied to execute the extractions:

| | |
|---|---|
| Temperature | 150° C. |
| Static time | 90 min |
| Rinse volume | 220 sec |
| Static cycle | 1 |
| Reduce relief | off |
| Preheat time | 0 min |
| Preheat purge | off |
| Bypass heatup | off |

This extraction procedure is repeated 10 times and the collected brown solutions are mixed together. DMSO (60 mL) is added. Solution is concentrated under vacuum with external bath temperature set at 65° C., once most of water is evaporated, xylan is precipitated adding ethanol (1500 mL) under stirring. Stirring is continued for 1 hour and the product is filtered and washed with ethanol (two times, each one with 200 mL). After drying 29 g beech xylan are obtained.

Example 5

Selective Deacetylation of Xylan

Water (160 mL) and beech xylan (10 g) are mixed under stirring. The temperature is brought to 10° C. with a thermostatic bath. Sodium hydroxide 30% water solution is added till pH=11.0. Stirring is continued and temperature is maintained while sodium hydroxide 5% water solution is automatically added to maintain pH in the range between pH=11.0 and pH=11.1. The addition of sodium hydroxide solution is controlled the by means of a pH-stat system.

After 8 hours in total 10.6 g of the sodium hydroxide 5% solution were added. Acetic acid is added for neutralization. To the reaction mixture DMSO (20 mL) is added and the mixture is concentrated under vacuum till residual weight is about 35 g. The concentrated solution is added to ethanol (600 mL). A precipitate is formed, the slurry is stirred at room temperature for 2 hours and filtered. After drying 7.8 g of slightly colored powder are obtained.

Starting material (beech xylan) and the obtained selectively deacetylated xylan product are both analyzed for acetyl distribution by $^1$H-NMR. Acetyl group linked to a xylose unit bearing also a 4-O-methyl-glucuronic acid unit resulted to be 10% of total acetyl groups in the starting material and 83% of total acetyl groups in the selectively deacetylated product.

Example 6

Isomerization of Beech Xylan

Beech xylan of example 5 (5 g) is mixed with 50 mL water and 50 mL pyridine. The mixture is heated to reflux and temperature maintained under stirring for 8 hours. Solvent is removed under vacuum until residual weight is 10 g. Ethanol is added and again solvent is removed under vacuum until residual weight is about 10 g. Ethanol (150 mL) is added and the mixture is stirred at room temperature for 2 hours. The solid is filtered and dried under vacuum at 45° C. obtaining 4.3 g. Both starting material (beech xylan) and product (isomerized beech xylan) were analyzed for monosaccharide composition: the result for lyxose in the starting material was 0 (lyxose not detectable) and 0.9% in the obtained product.

The invention claimed is:

1. Process for the preparation of a polysaccharide composed of D-xylose units of formula (III) linked together via beta 1,4 glycosidic bonds

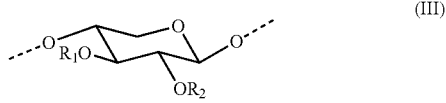

wherein
R₁ is hydrogen or acetyl,
R₂ is hydrogen, acetyl or a 4-O-methyl glucuronic acid unit,
wherein, when R₂ is a 4-O-methyl glucuronic acid unit, the R₁ group on the same saccharide unit is defined as G, wherein G is hydrogen or acetyl,
and wherein the sugar unit at the reducing end of the polysaccharide is, lyxose or xylulose, said process comprising the following steps:
a) selectively deacetylating xylan extracted from beech wood; and
b) isomerizing the selectively deacetylated xylan achieved in step a)
or the following steps:
c) isomerizing xylan extracted from beech wood; and
d) selectively deacetylating isomerized xylan achieved in step c).

2. The process according to claim 1 wherein step a) or step d) is performed in the presence of a basic reagent.

3. The process according to claim 2 wherein step a) or step d) is performed in aqueous environment at a pH comprised in the range between pH=8 and pH=12.

4. The process according to claim 1 wherein-step b) is performed by heating deacetylated xylan achieved in step a) in presence of pyridine.

5. The process according to claim 1 wherein step c) is performed by heating xylan extracted from beech wood in presence of pyridine.

6. The process according to claim 4 wherein that step b) or step c) is performed in the presence of at least one additional substance selected from alumina, aluminum acetate, calcium chloride and calcium acetate.

7. The process according to claim 1 wherein step a) and step b) are performed in "one-pot".

8. The process according to claim 7 wherein the "one-pot" reaction is performed in the presence of a basic reagent and of at least one substance containing polyvalent metals in aqueous environment.

9. The process according to claim 8 wherein said at least one substance containing polyvalent metals is selected from the group consisting of-calcium chloride, calcium acetate and aluminum acetate.

10. The process according to claim 1 further comprising the step of converting the polysaccharide into pentosan polysulfate by sulfation reaction.

11. The process according to claim 10 further comprising the step of converting pentosan polysulfate into a pharmaceutically acceptable salt.

12. Process according to claim 1, wherein the polysaccharide has the formula (II)

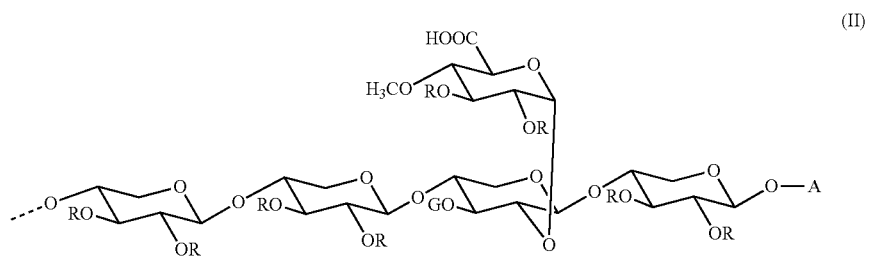

wherein
R is hydrogen or acetyl,
G is hydrogen or acetyl,
A is a, lyxose or xylulose unit.

13. A polysaccharide composed of D-xylose units of formula (III) linked together via beta 1,4 glycosidic bonds

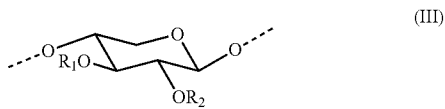

wherein
R₁ is hydrogen or acetyl,
R₂ is hydrogen, acetyl or a 4-O-methyl glucuronic acid unit,
wherein, when R₂ is a 4-O-methyl glucuronic acid unit, the R₁ group on the same saccharide unit is defined as G, wherein G is hydrogen or acetyl,
and wherein the sugar unit at the reducing end of such polysaccharide is, lyxose or xylulose.

14. A polysaccharide of formula (II)
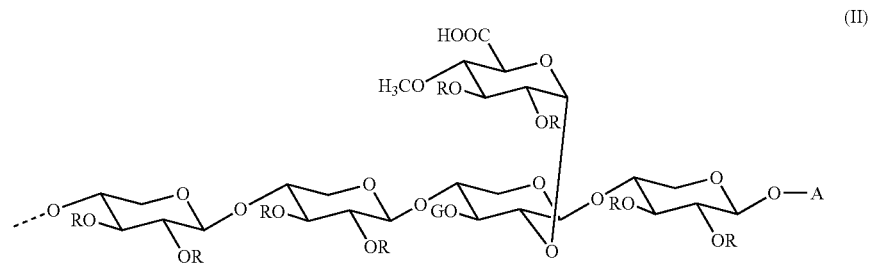
wherein
R is hydrogen or acetyl,
G is hydrogen or acetyl,
A is a, lyxose or xylulose unit.
* * * * *